(12) United States Patent
Chow et al.

(10) Patent No.: US 6,528,291 B1
(45) Date of Patent: Mar. 4, 2003

(54) ACTIVATED INORGANIC SLIDE HAVING ALDEHYDE GROUPS DEPOSITED BY PLASMA DEPOSITION

(75) Inventors: Zu-Sho Chow, Hsinchu Hsien (TW); Jia-Huey Tsao, Taoyuan (TW); Wen-Hsun Kuo, Tainan (TW); Chih-Wei Ho, Miaoli Hsien (TW); Bor-Iuan Jan, Pingtung (TW); Chao-Chi Pan, Hsinchu (TW); Yao-Sung Chang, Hsinchu (TW); Cheng-Tao Wu, Tainan (TW); Yu-Ching Liu, Taichung Hsien (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 09/658,945

(22) Filed: Sep. 11, 2000

(30) Foreign Application Priority Data

May 12, 2000 (TW) .......................... 89109126 A

(51) Int. Cl.⁷ .................. C12N 11/14; C12N 11/08; G01N 33/551; C07K 17/14; C07K 17/08
(52) U.S. Cl. ................ 435/176; 435/180; 435/181; 436/524; 436/527; 436/531; 436/532; 530/402; 530/811; 530/815; 530/816
(58) Field of Search ................ 435/174, 176, 435/177, 180, 181; 525/54.1; 530/402, 811, 815, 816; 436/524, 527, 531, 532

(56) References Cited

U.S. PATENT DOCUMENTS 5,028,657 A    7/1991   Hsu et al. .................. 425/54.1
5,554,501 A    9/1996   Coassin et al. ................ 435/6

FOREIGN PATENT DOCUMENTS

JP           63185383        7/1988

OTHER PUBLICATIONS

Chen, Fang C. & Lackritz, Hilary S.; In–Situ Nonlinear Optical Studies of Photopolymerization of Gas Phase Acrolein onto Metallic Substrates; American Chemical Society, Sep. 1, 1997, vol. 30, No. 20, p 5986–5996.
Leich, Megan A. et al.; Pulsed Plasma Polymerization of Benzaldehyde for Retention of the Aldehyde Functional Group; American Chemical Society, Mar. 3, 1998, vol. 31, No. 22, p. 7618–7626.
Griesser, Hans J. et al.; Surface Immobilization of Synthetic Proteins Via Plasma Polymer Interlayers; Materials Research Society, 1999, vol. 544, p. 9–20.

*Primary Examiner*—David M. Naff
(74) *Attorney, Agent, or Firm*—Fei-Fei Chao; Venable, Baetjer, Howard & Civiletti, LLP

(57) ABSTRACT

A method is provided for preparing an active slide, including introducing a monomer containing an aldehyde group, or a mixture of a monomer containing an aldehyde group and an acidic functional group provider into a plasma chamber; and depositing the aldehyde group and acidic functional group onto the surface of an organic or inorganic matrix using plasma deposition to form a slide comprising a layer of polymerized actively functional groups thereon. The aldehyde groups and negatively charged groups are deposited on the surface of the active slide, such that the bio-molecules bound thereto possess the properties of an inducible orientation and thus form a mono-layer.

28 Claims, 4 Drawing Sheets

(4 of 4 Drawing Sheet(s) Filed in Color)

(A)  (B)

US 6,528,291 B1

ACTIVATED INORGANIC SLIDE HAVING ALDEHYDE GROUPS DEPOSITED BY PLASMA DEPOSITION

RELATED APPLICATION

This application claims the priority of Taiwanese Application Ser. No. 89109126, filed on May 12, 2000, which is herein incorporated by reference.

BACKGROUND OF THE INVENTION

1. Field of the Invention

The present invention relates to an active slide and the preparation method thereof. More particularly, the present invention relates to the use of a plasma deposition method to deposit aldehyde groups and negatively charged groups on a matrix to form an active slide containing functional groups thereon.

2. Description of the Related Arts

There are many protein immobilization methods which are available to immobilize protein on different kinds of materials. For example, chemical activation, entrapment and crosslinking are well known in the art. However, these conventional methods suffer from many drawbacks, such as forming products of low stability and low activity and the inability of any one method to work well with a variety of proteins.

In conventional processes, the surface of the matrix has to be treated with silanization. In this treatment, the surface of the matrix is activated based on its material, followed by crosslinking via a crosslinker such as glutaldehyde to immobilize biomaterials on the matrix. The shortcomings of the method include long period of reaction time and low reaction efficiency. Thus, the resulting immobilized biomaterials are usually low activity. JP Nos. 59-28476 and 61-87699 disclose the technology of immobilizing proteins on a matrix using plasma activation. In this method, free radicals are activated on both the matrix surface and protein to form a covalent bonding between them. U.S. Pat. Nos. 5,028,657, 5,171,779 and 5,306,768 disclose the method for the activation of protein and functional groups on the polymer material using plasma technology to facilitate the immobilization. In these prior arts, plasma is used only for the activation of the matrix surface and protein to generate free radicals to immobilize proteins therein.

Another immobilization method is to activate free radicals from the matrix surface in a plasma chamber, and then introduce aldehyde groups to provide a surface useful for covalent bonding. Thus, proteins are covalently bound to the surface of the matrix. This has been disclosed in JP No. 63-185383 and Hans J. Griesser et al, 1999, *Mat. Res. Soc. Symp. Proc.* 544:9–20.

In these prior arts, the deposition of aldehyde groups directly onto a matrix using plasma deposition to form a polymerized layer of actively functional groups is not disclosed. In addition, the co-deposition of negatively charged groups (e.g. acidic functional groups) onto the matrix to improve the orientational bioactivity of the bio-materials during bonding thereto is not disclosed.

SUMMARY OF THE INVENTION

It is therefore a primary object of the present invention to provide a method for preparing an active slide, comprising: (a) introducing a monomer containing an aldehyde group, or a mixture of a monomer containing an aldehyde group and an acidic functional group provider into a plasma chamber; and (b) depositing said aldehyde group and acidic functional group onto the surface of a matrix using plasma deposition to form a slide comprising a layer of polymerized actively functional groups thereon. Prior to introducing the monomer and/or acidic functional group provider into the chamber, a cleaning step for the matrix and chamber may be performed.

Another aspect of the present invention provides an active slide, comprising: (i) a matrix; and (ii) a layer of actively functional groups polymerized by a monomer containing an aldehyde group using plasma deposition, wherein said layer is deposited onto the matrix.

Still another aspect of the present invention provides an active slide with a negatively charged surface, comprising: (i) a matrix; and (ii) a layer of actively functional groups polymerized by a mixture of a monomer containing an aldehyde group and an acidic functional group provider using plasma deposition, wherein said layer is deposited onto the matrix.

Yet still another aspect of the present invention provides an active slide microarray, comprising: (i) a matrix; (ii) a layer of actively functional groups polymerized by a monomer containing an aldehyde group using plasma deposition, wherein said layer is deposited onto the matrix; and (iii) a biologically active material, which is immobilized onto said layer of actively functional groups.

Still another aspect of the present invention provides an active slide microarray with a negatively charged surface, comprising: (i) a matrix; (ii) a layer of actively functional groups polymerized by a mixture of a monomer containing an aldehyde group and an acidic functional group provider using plasma deposition, wherein said layer is deposited onto the matrix; and (iii) a biologically active material, which is immobilized onto said layer of actively functional groups.

The matrix used herein may be an organic or inorganic matrix (i.e. matrix-independent). However, if an inorganic matrix is employed, an interlayer polymerized by a monomer of an organic compound containing silicon is deposited onto the inorganic matrix, and is located between the inorganic matrix and the layer of actively functional groups.

BRIEF DESCRIPTION OF THE DRAWINGS

This patent file contains at least one drawing executed in color. Copies of this patent with color drawing(s) will be provided by the Patent and Trademark Office upon request and payment of the necessary fee.

The present invention will be more fully understood and further advantages will become apparent when reference is made to the following description of the invention and the accompanying drawings in which.

DETAILED DESCRIPTION OF THE INVENTION

Figure 1:
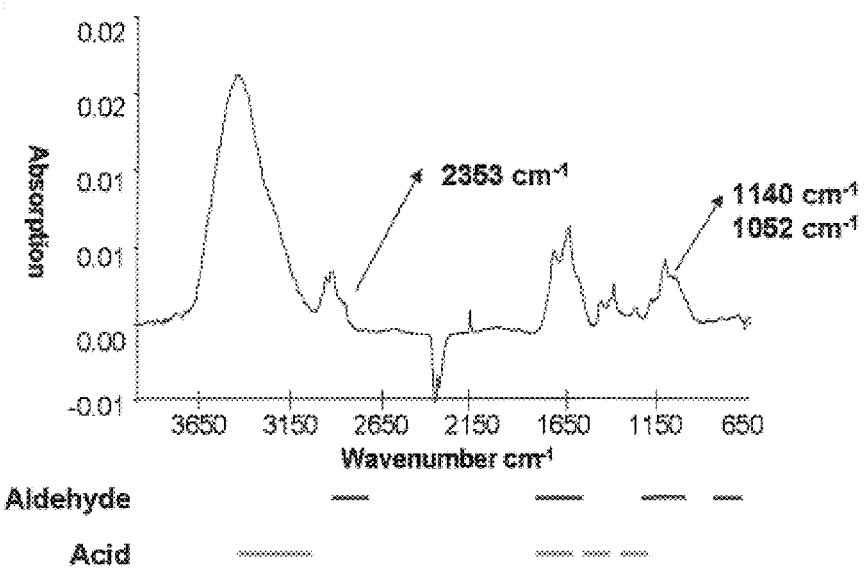
FIG. 1 is a diagram of surface-FTIR spectrum showing the presence of aldehyde groups and carboxyl groups after plasma deposition.

The present invention is directed to a method for preparing an active slide, wherein the active aldehyde groups and/or negatively charged groups are formed directly on the matrix using plasma deposition. The covalent bonding reaction is thus reduced to a one-step reaction compared with the conventional method, and it is therefore to save the time and elevate the efficiency of the immobilization. In addition, the negatively charged groups deposited on the surface of the active slide benefit the biologically active material to have an inducible orientation and form a monolayer.

As used herein, the term "actively functional groups" shall be taken to refer to any functional groups linked by covalent bonding that are useful for further binding to the bio-molecules, and thus include aldehyde groups and/or negatively charged groups.

In accordance with the present invention, there is provided a method for preparing an active slide, comprising: (a) introducing a monomer containing an aldehyde group, or a mixture of a monomer containing an aldehyde group and an acidic functional group provider into a plasma chamber; and (b) depositing said aldehyde group and acidic functional group onto the surface of a matrix using plasma deposition to form a slide comprising a layer of polymerized actively functional groups thereon. In this method, the type of the matrix is not limited, and can include an organic or inorganic matrix. Organic matrices include a polymer polymerized by an organic molecule. Suitable organic molecules include, for example, monomer of ethylene, propylene, ester, acrylic acid, acrylate, alkyl acrylic acid, or alkyl acrylate. In one embodiment of the present invention, the organic matrix is selected from polymethyl methacrylate (PMMA). Inorganic matrices include, but are not limited to silicon wafer, ceramic material, glass or metal.

According to the method of the present invention, the matrix surface and plasma chamber can be cleaned prior to the plasma deposition to prevent the deposition of impurities or contaminants on the matrix surface. The cleaning step is performed by pretreatment with a solvent and/or sonication, based on the material of the matrix. Suitable solvents include, but are not limited to, surfactant, water, alcohol or acetone.

If an inorganic matrix is employed, an interlayer polymerized by a monomer of an organic compound containing silicon is deposited onto the inorganic matrix prior to introducing aldehyde group and acidic functional group provider (e.g. $CO_2$) into a plasma chamber. An interlayer is thus formed between the inorganic matrix and the layer of actively functional groups to provide an environment for subsequent deposition. The process for forming the interlayer is not limited to the plasma deposition described in the present invention, others such as chemical method or any method conventionally used in this art is also contemplated. The organic compound containing silicon includes, for example, the volatile monomer of hexamethyl disilazane (HMDSZ) or hexamethyl disiloxane (HMDSO).

According to the method of the present invention, aldehyde groups and negatively charged groups (e.g. acidic functional groups) are introduced into the plasma chamber and deposited onto a matrix using plasma deposition to form an active slide with a layer of actively functional groups. In this method, a monomer containing an aldehyde group includes, but is not limited to the volatile monomer of acrolein or benzaldehyde. Moreover, the negatively charged groups used herein are acidic functional groups. Those skilled in this art should be aware that the use of such negatively charged groups can provide the bioactive orientation of the bio-materials after bonding on the active slide, such that a biologically active material can be formed as a mono-layer (as described below). The selection of the negatively charged groups therefore includes, but is not limited to carboxyl group ($—COO^-$), phosphate group ($—PO_4^{3-}$) or sulfonate group ($—SO_3^{2-}$) The method for generating negatively charged groups includes plasma deposition. In addition, other methods such as graft co-polymerization are within the scope of the present invention.

The present invention clearly contemplates the application of the active slide to, for example, a microarray and the use therefor. The microarray comprises a biologically active material, which is immobilized onto the layer of actively functional groups described above. The immobilization is achieved by way of contacting the bio-molecules with the active slide of the present invention. The interfacial immobilization reaction between the aldehyde groups of the active slide and the amine groups of the bio-molecules, (which the amines are present in the protein itself or in a chemically-modified entity) causes formation of interfacial Schiff-base bonds. In one embodiment of the present invention, Schiff-base linkages ($—CH=N—$) are subsequently treated by reductive amination, preferably by treatment with a reducing agent, for example, cyanoborohydride to form $—CH_2—NH—$ bonds. Such reductive amination improves the strength of covalent immobilization.

Bio-molecules used as the biologically active material that are suitable for use in the invention include nucleic acid, oligonucleotide, peptide nucleic acid (PNA), antigen, antibody, enzyme or protein. Stable Schiff-base linkages are formed after such bio-molecules are reacted with the aldehyde groups of the active slide. As compared with the prior arts in which the bonding is created via two-step reaction mostly, i.e. by the silane-based polymer and followed by adding the crosslinker (e.g. glutaldehyde), such reaction is reduced to one-step reaction in the present invention, thereby substantially decreasing the time for the immobilization reaction and increasing its efficiency.

Another feature of the present invention is to co-deposit aldehyde groups and negatively charged groups such as carboxyl group, phosphate group or sulfonate group onto a matrix. Afterwards, the bio-molecules bound to this active slide possess the properties of an inducible orientation and thus form a mono-layer due to the interaction of the negatively charged groups. Because most of the bio-molecules are negatively charged, the repulsive forces generated between the negatively charged groups and the bio-molecules cause the bio-molecules to have a certain orientation and thus easily form a mono-layer.

Without intending to limit it in any manner, the present invention will be further illustrated by the following examples.

EXAMPLE 1

A glass matrix was washed sequentially with surfactant, deionized water, acetone, deionized water and alcohol under an environment of sonication. The cleaned glass matrix and KBr salt plate were placed in a plasma chamber. Argon was introduced therein at 0.08 Torr, applying a power of 50 W for 5 minutes for further cleaning. A mixture of argon and acrolein was fed at the pressure from 0.03 to 0.16 Torr, applying a power of 20 W for 5 minutes for deposition. The FTIR analysis was performed for the resulting KBr salt plate. The result is shown in FIG. 1.

EXAMPLE 2

Figure 2:
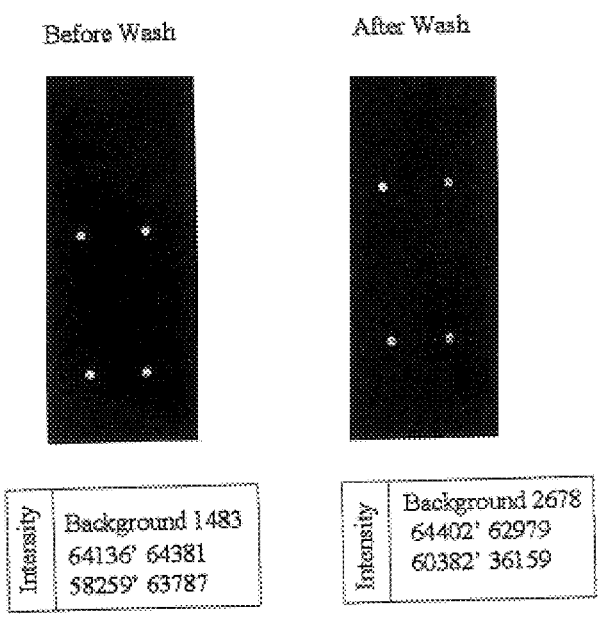
FIG. 2 is a diagram showing the immobilization efficiency of the active slide of the present invention.

A glass matrix was used in this example, and other conditions such as cleaning or plasma deposition were the same as Example 1. A synthetic oligonucleotide probe AP21 composed of 21 nucleotides in which the 3' end was labeled with fluorescence and the 5' end bore amine group, was immobilized to the active slide prepared in Example 1 to form Schiff-base linkages. The immobilization conditions were described as follows: 0.5 $\mu$M of AP21 in 10×SSC buffer (pH 3.0) was spotted on the active slide and incubated at 37° C. for 16 hours. The slides were prepared duplicated, wherein one was washed after immobilization, as follows: 0.2% SDS for 1 minute; rinsed with deionized water; $NaBH_{4(aq)}$ (1 g of $NaBH_4$ dissolved in 300 ml of PBS buffer and 100 ml of ethanol) for 5 minutes; rinsed with deionized water; and dried in the oven at 37° C. for 10 minutes. The fluorescence analyses were performed for the slides with and without washing (control) to monitor the immobilization efficiency. The result is shown in FIG. 2.

EXAMPLE 3

Figure 3:
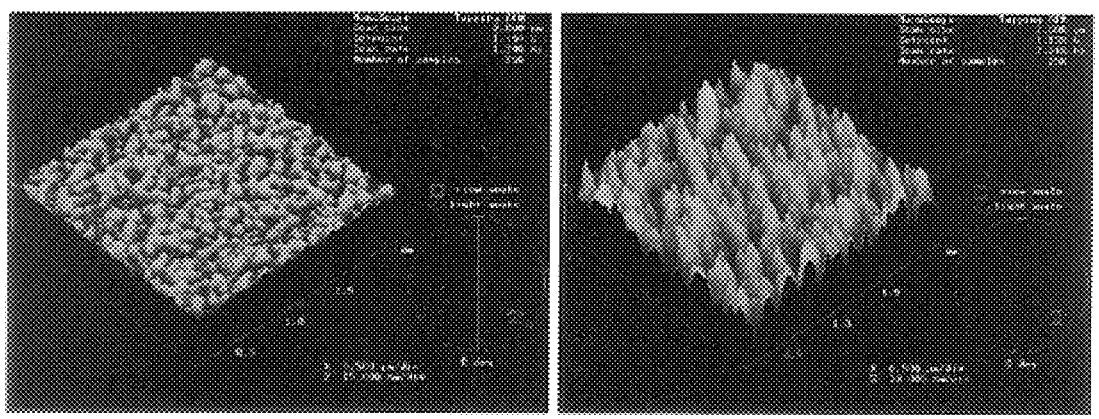
FIG. 3 is a diagram of surface-AFM analysis, showing (A): the deposition of aldehyde groups on the silicon wafer surface; and (B): the binding of the probe composed of 50 oligonucleotides to the silicon wafer surface containing aldehyde groups at pH 7.0.

A silicon wafer was used as the matrix in this example, and other conditions such as cleaning or plasma deposition were the same as Example 1. A synthetic oligonucleotide probe AP50 composed of 50 nucleotides with amine group at the 5' end, was immobilized to the active slide prepared in Example 1 to form Schiff base linkages. The immobilization conditions were described as follows: 2 $\mu$M of AP50 (pH 7.0) was spotted on the active slide and incubated at 37° C. for 16 hours. The AFM-surface analysis was performed. The result is shown in FIG. 3.

EXAMPLE 4

Figure 4:
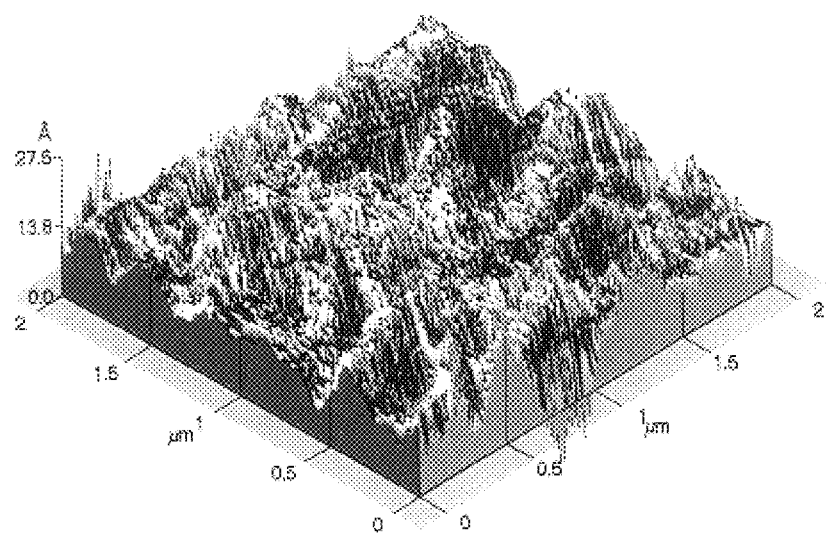
FIG. 4 is a diagram of surface-AFM analysis, showing the binding of the probe composed of 50 oligonucleotides to the silicon wafer surface containing aldehyde groups at pH 3.0.

In this Example, all parameters were the same as Example 3, except that the immobilization condition was pH 3.0. The AFM-surface analysis was performed. The result is shown in FIG. 4.

EXAMPLE 5

Figure 5:
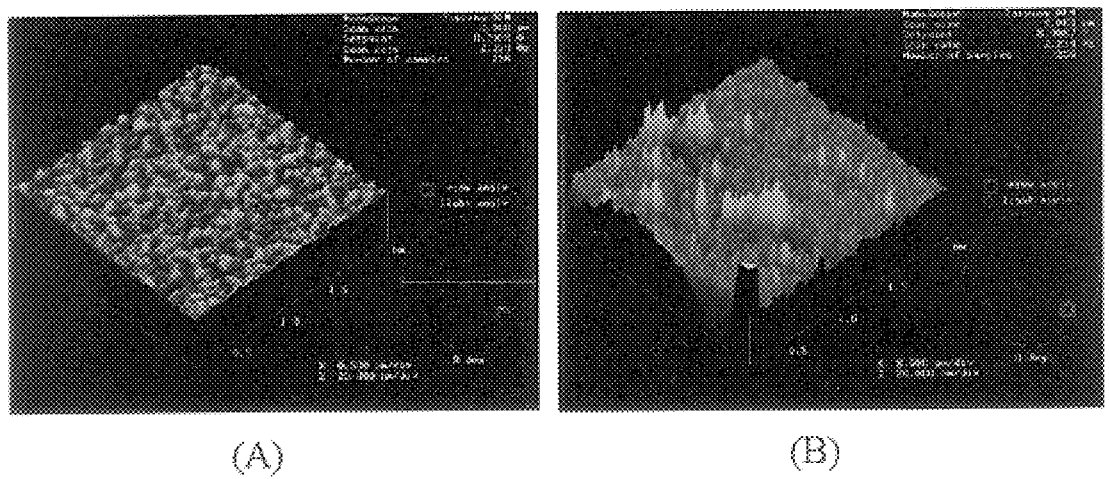
FIG. 5 is a diagram of surface-AFM analysis, showing (A): the deposition of aldehyde groups and carboxyl groups on the silicon wafer surface; and (B): the binding of the probe composed of 26 oligonucleotides to the silicon wafer surface containing aldehyde groups and carboxyl groups at pH 7.0.

In this Example, all parameters were the same as Example 3, except that the carbon dioxide ($CO_2$) was introduced instead of argon. A synthetic oligonucleotide probe AP26 composed of 26 nucleotides, with amine group at the 5' end, was immobilized to the active slide prepared in Example 1 to form Schiff base linkages. The immobilization conditions were the same as Example 3. The AFM-surface analysis was performed. The result is shown in FIG. 5.

EXAMPLE 6

Figure 6:
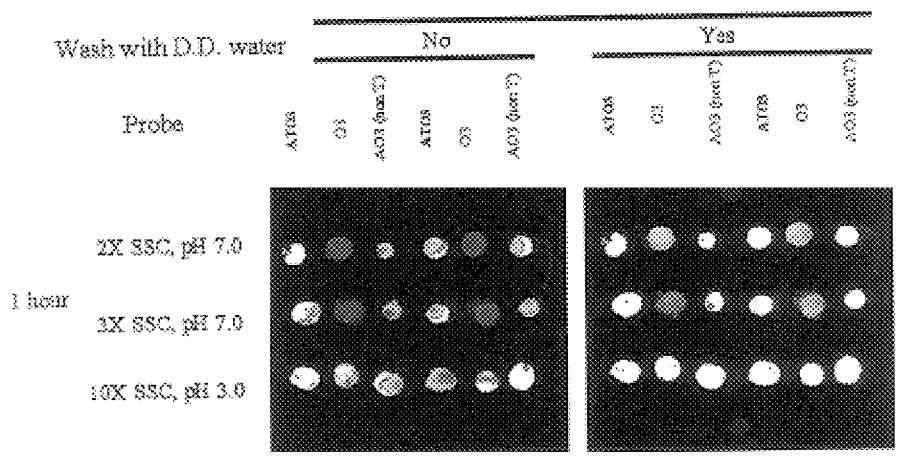
FIG. 6 is a diagram showing the specificity of the bio-molecules to the active slide of the present invention.

A glass matrix was used in this example, and other conditions such as cleaning or plasma deposition were the same as Example 1. The oligonucleotide probes used in this example were $AO_3$ (composed of 29 nucleotides with amine group at the 5' end); $O_3$ (composed of 29 nucleotides without amine group at the 5' end); and $ATO_3$ (composed of 15 thymidine bases and the same 29 nucleotides as set forth above with amine group at the 5' end), respectively. The probe used for labeling hybridization reaction was the complementary sequence thereto, wherein the 5' end was labeled with fluorescence. The immobilization conditions were 2×SSC, pH 7.0; 3×SSC, pH 7.0; and 10×SSC, pH 3.0, respectively, for 1 hour. The hybridization reaction was performed for 4 hours. The fluorescence analyses were performed for the slides with and without washing (control) to monitor the immobilization efficiency. The result is shown in FIG. 6.

EXAMPLE 7

Figure 7:
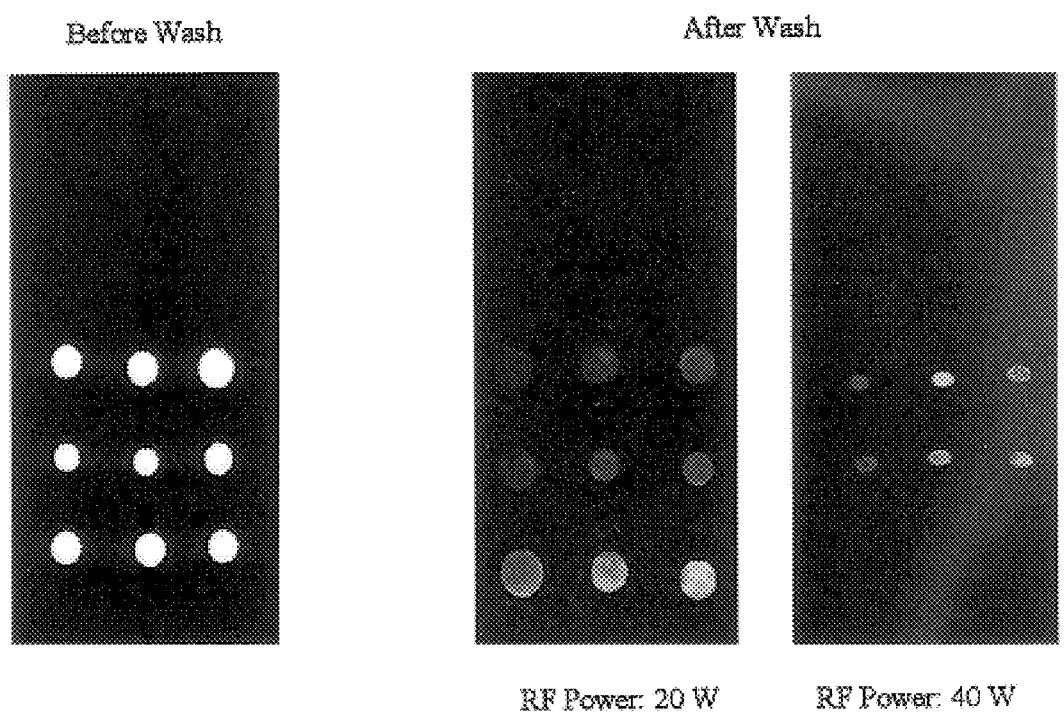
FIG. 7 is a diagram showing the immobilization efficiency of the active slide prepared from organic matrix (PMMA).

In this Example, an organic material of polymethyl methacrylate (PMMA) was used as the matrix, applying a power of 20 W and 40 W for deposition, respectively. Other conditions such as cleaning or plasma deposition were the same as Example 1. A synthetic oligonucleotide probe AP21 composed of 21 nucleotides, in which the 3' end was labeled with fluorescence and the 5' end bore amine group, was immobilized to the organic slide with actively functional groups to form Schiff-base linkages. The immobilization conditions were described as follows: 0.5 $\mu$M of AP21 in 10×SSC buffer (pH 7.0) was spotted on the active slide and incubated at 37° C. for 16 hours. The slides were prepared duplicated, wherein one was washed after immobilization, as follows: 0.2% SDS for 1 minute; rinsed with deionized water; $NaBH_{4(aq)}$ (1 g of $NaBH_4$ dissolved in 300 ml of PBS buffer and 100 ml of ethanol) for 5 minutes; rinsed with deionized water; and dried in the oven at 37° C. for 10 minutes. The fluorescence analyses were performed for the slides with and without washing (control) to monitor the immobilization efficiency. The result is shown in FIG. 7.

Referring to FIG. 1, FTIR-surface analysis shows the presence of aldehyde groups and carboxyl groups on the surface of the active slide after plasma deposition.

It is clearly shown from FIG. 2 that the probe immobilized on the active slide maintains at least 60% of immobilization efficiency after washing, revealing the stable bonding between bio-molecules and a layer of aldehyde groups deposited by the present invention.

Referring to FIG. 3(A), it is clearly shown that the aldehyde groups are homogeneously deposited onto the surface of silicon wafer. FIG. 3(B) shows the probe composed of 50 nucleotides (about 170Å in height) is immobilized on the silicon wafer containing aldehyde groups, indicating the arrangement of the oligonucleotide probe has a certain orientation.

Comparing with FIG. 5(A), the aldehyde groups and carboxyl groups are co-deposited onto the surface of silicon wafer. FIG. 5(B) shows the probe composed of 26 nucleotides is immobilized thereon. Due to the introduction of carboxyl groups, the amount of aldehyde groups deposited was decreased; however, the arrangement of the oligonucleotide probe also has a certain orientation.

Referring to FIGS. 3–5, it is shown that such orientation is not only caused by the repulsive force among the oligonucleotide molecules, but prominently due to the negative-charge existence of the carboxyl groups. In addition, the negative charges can be adjusted dependent on the pH environment.

Referring to FIG. 6, the differences among three probes are that $AO_3$ bears an amine group at the 5' end, whereas $O_3$ is without an amine group. The amine group at the 5' end of $ATO_3$ is ligated with 15 bases of thymidine not bearing amine group. Three kinds of probe were immobilized onto the slide at pH 3.0 and 7.0, respectively. From the result of $O_3$ probe, the poor bonding efficiency was observed due to the lack of an amine group at the 5' end. Other probes with amine group at the 5' end possess excellent bonding efficiency, even though there is an interval sequence without an amine group. This indicates the specificity of the bonding of the target molecule can be elevated markedly according to the active slide of the present invention.

A slide made of organic material (e.g. PMMA) can also be used for immobilization. Referring to FIG. 7, it is also shown that excellent bonding efficiency is present between bio-molecules and the organic slide containing the actively functional groups, indicating the matrix is independent (i.e. the matrix can be organic or inorganic material) according to the present invention.

While the invention has been particularly shown and described with the reference to the preferred embodiment thereof, it will be understood by those skilled in the art that various changes in form and details may be made without departing from the spirit and scope of the invention.

What is claimed is:

1. An activated slide comprising:
   (i) an inorganic slide;
   (ii) an interlayer polymerized by a monomer of an organic compound containing silicon using plasma deposition, wherein said interlayer is deposited onto said inorganic slide; and
   (iii) a layer of actively functional groups polymerized by a monomer containing an aldehyde group using plasma deposition, wherein said layer is deposited onto said interlayer.

2. The activated slide as claimed in claim 1, wherein said inorganic slide comprises silicon wafer, ceramic material, glass or metal.

3. The activated slide as claimed in claim 1, wherein said organic compound containing silicon comprises the volatile monomer of hexamethyl disilazane or hexamethyl disiloxane.

4. The active slide as claimed in claim 1, wherein said monomer containing an aldehyde group comprises the volatile monomer of acrolein or benzaldehyde.

5. An activated slide with a negatively charged surface comprising:
   (i) an inorganic slide;
   (ii) an interlayer polymerized by a monomer of an organic compound containing silicon using plasma deposition, wherein said interlayer is deposited onto said inorganic slide; and
   (iii) a layer of actively functional groups polymerized by a mixture of a monomer containing an aldehyde group and an acidic functional group provider using plasma deposition, wherein said layer is deposited onto said interlayer.

6. The activated slide as claimed in claim 5, wherein said inorganic slide comprises silicon wafer, ceramic material, glass or metal.

7. The active slide as claimed in claim 5, wherein said organic compound containing silicon comprises the volatile monomer of hexamethyl disilazane or hexamethyl disiloxane.

8. The activated slide as claimed in claim 5, wherein said monomer containing an aldehyde group comprises a volatile monomer of acrolein or benzaldehyde.

9. The activated slide as claimed in claim 5, wherein said acidic functional group comprises carboxyl group, phosphate group or sulfonate group.

10. An activated slide microarray comprising:
    (i) an inorganic slide;
    (ii) an interlayer polymerized by a monomer of an organic compound containing silicon using plasma deposition, wherein said interlayer is deposited onto said inorganic slide;
    (iii) a layer of actively functional groups polymerized by a monomer containing an aldehyde group using plasma deposition, wherein said layer is deposited onto said interlayer; and
    (iv) a biologically active material, which is immobilized onto said layer of actively functional groups.

11. The microarray as claimed in claim 10, wherein said inorganic slide comprises silicon wafer, ceramic material, glass metal.

12. The microarray as claimed in claim 10, wherein said organic compound containing silicon comprises the volatile monomer of hexamethyl disilazane or hexamethyl disiloxane.

13. The microarray as claimed in 10, wherein said monomer containing an aldehyde group comprises the volatile monomer of acrolein or benzaldehyde.

14. The microarray as claimed in claim 10, wherein said biologically active material comprises nucleic acid, oligonucleotide, peptide nucleic acid, antigen, antibody, enzyme or protein.

15. An activated slide microarray with a negatively charged surface comprising:
    (i) an inorganic slide;
    (ii) an interlayer polymerized by a monomer of an organic compound containing silicon using plasma deposition, wherein said interlayer is deposited onto said inorganic slide;
    (iii) a layer of actively functional groups polymerized by a mixture of a monomer containing an aldehyde group and an acidic functional group provider using plasma deposition, wherein said layer is deposited onto said interlayer; and
    (iv) a biologically active material, which is immobilized onto said layer of actively functional groups.

16. The microarray as claimed in claim 15, wherein said inorganic slide comprises silicon wafer, ceramic material, glass or metal.

17. The microarray as claimed in claim 15, wherein said organic compound containing silicon comprises the volatile monomer of hexamethyl disilazane or hexamethyl disiloxane.

18. The microarray as claimed in claim 15, wherein said monomer containing an aldehyde group comprises the volatile monomer of acrolein or benzaldehyde.

19. The microarray as claimed in claim 15, wherein said acidic functional group comprises carboxyl group, phosphate group or sulfonate group.

20. The microarray as claimed in claim 15, wherein said biologically active material comprises nucleic acid, oligonucleotide, peptide nucleic acid, antigen, antibody, enzyme or protein.

21. The microarray as claimed in claim 15, wherein said biologically active material is characterized by having an inducible orientation and forming a monolayer.

22. A method for preparing an activated slide comprising:

(a) introducing an organic compound containing silicon into a plasma chamber and forming an interlayer on the surface of an inorganic slide using plasma deposition; and (b) introducing a mixture of a monomer containing an aldehyde group and an acidic functional group provider into the plasma chamber, and depositing said aldehyde group and said acidic functional group onto the surface of said interlayer using plasma deposition to form said activated slide comprising a layer of polymerized actively functional groups thereon.

23. The method as claimed in claim 22, further comprising cleaning said inorganic slide and plasma chamber before step (a).

24. The method as claimed in claim 22, wherein said inorganic slide comprises silicon wafer, ceramic material, glass or metal.

25. The method as claimed in claim 22, wherein said organic compound containing silicon comprises the volatile monomer of hexamethyl disiulazane or hexamethyl distiloxane.

26. The method as claimed in claim 23, wherein the cleaning step is performed by pretreatment with an solvent and/or sonication.

27. The method as claimed in and claim 22, wherein said monomer containing an aldehyde group comprises the volatile monomer of acrolein or benzaldehyde.

28. The method as claimed inand claim 22, wherein said acidic functional group comprises carboxyl group, phosphate group or sulfonate group.

* * * * *